United States Patent [19]

McGredy

[11] Plant 4,993

[45] Mar. 15, 1983

[54] ROSE PLANT

[76] Inventor: Samuel D. McGredy, P.O. Box 14100, Panmure, Auckland, New Zealand

[21] Appl. No.: 283,539

[22] Filed: Jul. 15, 1981

[51] Int. Cl.[3] ..... A01H 5/00

[52] U.S. Cl. ..... Plt./22

[58] Field of Search ..... Plt/22

*Primary Examiner*—Robert E. Bagwill

*Attorney, Agent, or Firm*—Vincent G. Gioia

[57] ABSTRACT

A new floribunda rose variety of carmine red flowers with light colored petal edges and flower center borne in large sprays.

1 Drawing Figure

1

The present invention relates to a new and distinct variety of rose plant of the floribunda rose class, which was originated by my crossing as seed and pollen parents, unnamed and unpatented seedlings of my creation.

Among the novel characteristics possessed by this new variety which distinguish it from its parents and all other varieties of which I am aware are flowers of unusual multi-coloring borne in large sprays. Flowers are carmine red with lighter colored distinct petal edge and lower petal section toward point of attachment. The flower's unique coloring with light colored edges and center and yellow "eye" (formed by stamens and pollen) give a hand painted effect. Asexual reproduction by budding of the new variety as performed in Kern County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (RHSCC). The terminology used in color description herein refers to plate numbers in the aforementioned color chart, e.g., "36D" is plate 36D of The Royal Horticultural Society Color Chart.

Parentage: Seedling.

*Seed parent.*—Unnamed seedling.

*Pollen parent.*—Unnamed seedling.

Class: Floribunda.

The following observations are made of specimens grown outdoors in Kern County, Calif. during the month of October.

FLOWER

Blooming habit: Continuous.

A. Bud:

(1) *Size.*—Small.

(2) *Form.*—High centered, long pointed.

(3) *Color.*—When sepals first divide — 36D, becoming quickly 55C to 55D.

(4) *Sepals.*—Simple, longer than bud, glabrous exterior, pilose interior.

2

(5) *Peduncle.*—Length — Medium. Aspect — straight. Strength — erect. Color — 146C.

B. Bloom:

(1) *Size.*—Average size when fully expanded — about 4½ inches.

(2) *Borne.*—5 to 12 to a spray.

(3) *Form.*—High centered at first opening quickly to a flat ruffled bloom preserving form longer than average.

(4) *Petalage.*—Number of petals under normal conditions — about 15.

(5) *Color.*—Relatively few petalled flowers open quickly to display ruffled petals of largely carmine 52B coloring but with distinct light 56C to 56D petal edge and lower petal section. The open bloom has attractive combination of light colored center and yellow "eye" (formed by stamens and pollen coloring), major carmine flower coloring of petals and light colored petal edge giving a total "hand painted" effect.

C. Petals:

(1) *Texture.*—Thick, heavy substance.

(2) *Appearance.*—Smooth with satiny sheen.

(3) *Form.*—High centered.

(4) *Arrangement.*—Regular.

(5) *Petaloids in center.*—Few.

(6) *Persistence.*—Drop off cleanly.

(7) *Fragrance.*—Slight, fruity.

(8) *Lasting quality.*—Long lasting on plant and as cut flower.

REPRODUCTIVE ORGANS

A. Stamens, filaments and anthers:

(1) *Arrangement.*—Stamens regular, arranged around styles, with anthers notched.

(2) *Color.*—19B.

B. Pollen:

*Color.*—17A.

C. Styles: Many, bunched, even length, hairy.

D. Stigmas:

*Color.*—20B, surface expanded.

E. Hips:

*Shape.*—globular.

*Size.*—Small.

*Color.*—24B.

*Do seeds protrude?*—No.

PLANT

A. Form: Compact, short, slightly spreading.

B. Growth: Vigorous, free branching.

*Height attained.*—About 25 to 30 inches.

C. Foliage: Compound 5 to 7 leaflets.

(1) *Size.*—Medium.

(2) *Quantity.*—Abundant with short internodes.

(3) *Color.*—New foliage: Upper side — near 59A. Under side — near 59B. Old foliage: Upper side — near 137B. Under side — near 137C.

(4) *Shape.*—Long, oval, pointed.

(5) *Texture.*—Upper side is leathery and under side is flat.

(6) *Edge.*—Serrate.

(7) *Serration.*—Light.

(8) *Leaf stem.*—Color — near 166B. Under side — near 145B.

(9) *Stipules.*—Short, simple, accuminate.

(10) *Resistance to disease.*—Blackspot — fair. Mildew — excellent. Rust — excellent.

D. Wood:

(1) *New wood.*—Color — near 176B. Bark — smooth.

(2) *Old wood.*—Color — near 147B. Bark — smooth.

E. Thorns:

(1) *Thorns.*—Quantity (main stalk): many. On laterals from stalk — few. Form — long pointed. Length — small. Color — near 46A. Position — distributed.

(2) *Prickles.*—None.

F. Winter hardiness: Good winter hardiness.

I claim:

1. A new and distinct variety of rose plant of the floribunda class, substantially as shown and described, characterized particularly by large (5 to 12 bloom) sprays of flowers of unusual coloration combining carmine petal coloring and light colored petal edges and flower centers.

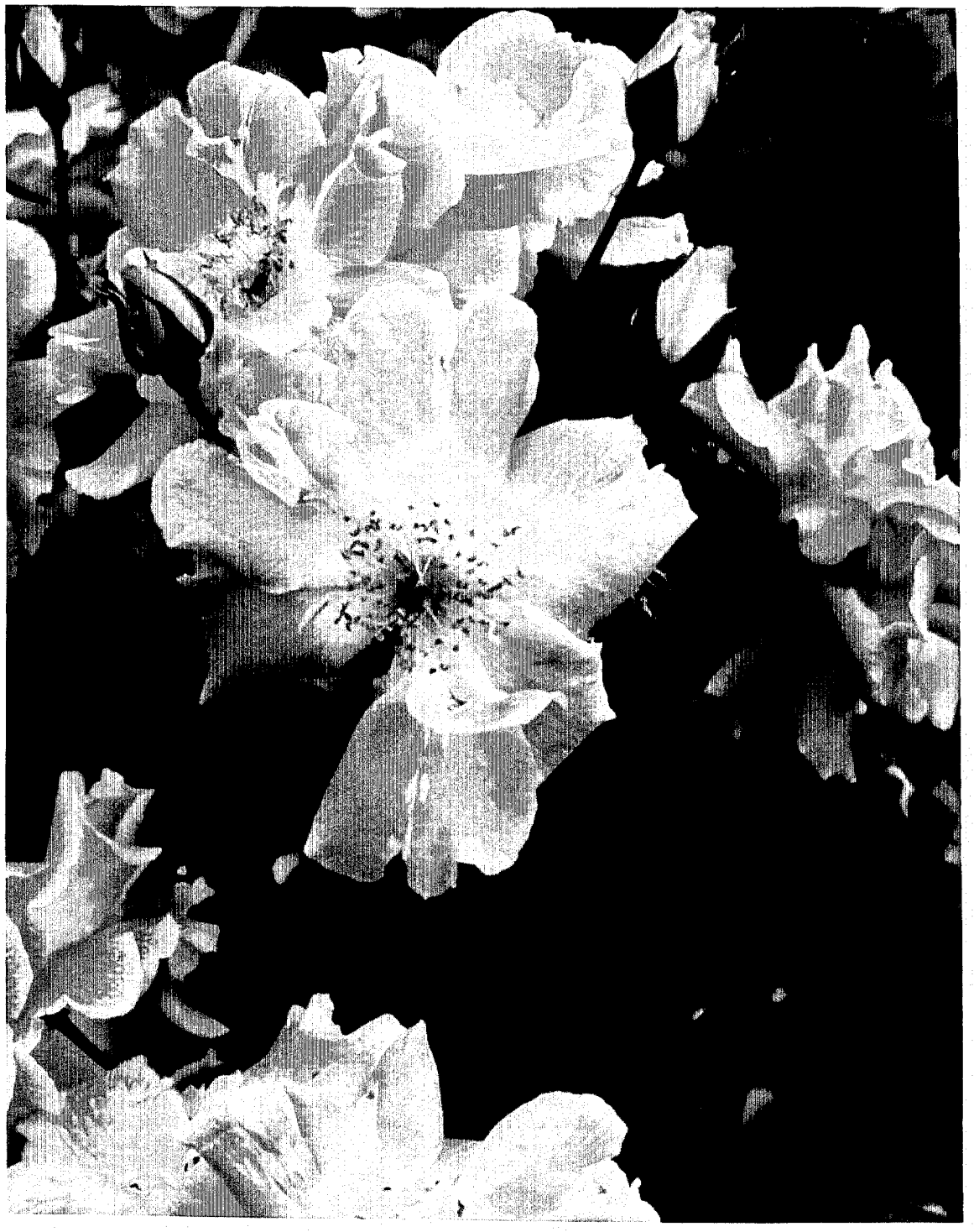

* * * * *